United States Patent [19]

McRae

[11] Patent Number: Plant 6,574

[45] Date of Patent: Jan. 31, 1989

[54] LILY PLANT NAMED 'HORNPIPE'

[75] Inventor: Edward A. McRae, Boring, Oreg.

[73] Assignee: Melridge, Inc., Aurora, Oreg.

[21] Appl. No.: 63,928

[22] Filed: Jun. 19, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler

[57] ABSTRACT

A new variety of hybrid lily plant particularly characterized by the vivid golden orange coloration of its flowers which have broad tepals with fluted margins and a complete lack of spotting, the flowers being of excellent form, large size and borne in large clusters with an upright orientation on straight, stately stems. The new plant is highly resistant to disease and shows high tolerance of virus; it is an excellent garden plant and the bulbs may be precooled and forced throughout the year for cut flower production.

1 Drawing Sheet

BACKGROUND OF THE INVENTION

This new variety of lily plant originated as a seedling selected from a group of seedlings planted by me at Sandy, Oreg., with seeds from a hybrid of my breeding efforts and resulting from my crossing the clonal cultivar 'Connecticut King' as the seed parent with the clonal cultivar 'Croesus' as the pollen parent, my object being to achieve the production of lilies in shades of gold and orange well suited to forcing for cut flower production out-of-season with such a variety of forcing time requirements that production may be accomplished throughout the year.

This particular seedling was selected for propagation and test because of its unusual broad tepalled flower form and clean, attractive coloration, and the selected seedling was asexually reproduced by me at Sandy, Oreg., by bulb scale propagation with such satisfactory results that successive generations were produced under my direction by bulb scale propagation and by natural propagation from bulblets and this work clearly demonstrated that the novel and distinctive characteristics of this new lily variety would hold true under asexual propagation from generation to generation and appeared to be firmly fixed.

The large size of the flowers of this new lily variety with their broad tepals and vivid gold-orange coloration with a complete lack of spotting appears to be a color pattern unique in this type of lily. In addition, the clone possesses to a high degree the desirable characteristics of hybrid vigor, great hardiness, and disease resistance, and work with this new variety has shown it to be well suited to forcing out-of-season when the bulbs are dug at the appropriate time and properly precooled. October-dug bulbs, properly precooled and potted in January, will flower under glass in western Oregon in an average of eighty to eighty-eight days with no supplementary lighting and at moderate greenhouse temperatures. Also, the clone is vigorous and a good grower and propagator, as observed at Sandy, Oreg.

DESCRIPTION OF THE DRAWING

This new variety of lily plant is illustrated by the accompanying photographic drawing, which shows the open bloom in full color and illustrates the flower form, tepal arrangement, and the novel and distinctive spotless, golden orange coloration, the colors shown being as close to those herein specified as is reasonably possible to obtain by conventional, professional photographic procedures.

DESCRIPTION OF THE NEW VARIETY

The following is a detailed description of my new variety of Asiatic hybrid lily with nomenclature according to The International Lily Register (The Royal Horticultural Society of London, England, Second Edition, 1969), and with color designations according to The R.H.S. Colour Chart of The Royal Horticultural Society published in 1966.

THE PLANT

Origin: Seedling.

Parentage:

*Seed parent.*—Lilium 'Connecticut King' (unpatented).

*Pollen parent.*—Lilium 'Croesus' (unpatented).

Classification:

*Horticultural.*—Division I-A, Upright Asiatic Hybrid Lily, according to The Horticultural Classification of Lilies by The Royal Horticultural Society of London, England.

Form: A single stem, erect and stately.

Height: About 90 to 110 cm. on stems produced by glasshouse forcing of bulbs of about 12 to 18 cm. in circumference, provided that the light levels are adequate. Low light levels may cause "stretching".

Growth: Vigorous and upright.

Foliage:

*Quantity.*—Abundant.

*Leaf size.*—About 6 to 12 cm. long and about 0.5 to 1.5 cm. wide.

*Leaf shape.*—Lanceolate with acuminate tip.

*Texture.*—Leathery.

*Aspect.*—Glossy.

*Color.*—Dark green, somewhat lighter on the lower side.

The bulb:

*Size.*—Various, ranging to 25 cm. in circumference in commercial use.

*Color.*—White.

THE BUD

Form: Long ovoid with obtuse apex.

Size: About 8 to 9 cm. long and about 7 cm. in circumference just prior to opening.

Opening rate: The bud opens slowly, taking about an hour in response to morning light.

Color: Orange, 25B-C, at the center of the bud; slightly lighter in color at the apex and base prior to opening and as the tepals begin to unfurl.

Peduncle:

*Length.*—About 4 to 6 cm. in average, but it may elongate somewhat if light levels are too low or if the bulbs have been improperly stored prior to forcing.

*Color.*—Medium green overlaid with light plum.

THE FLOWER

Blooming habit: Annually, once and profusely in mid-season.

Size: About 16 to 19 cm. in diameter.

Borne: In a single compact raceme having nine to twelve buds on a stem, from a bulb of about 12 to 16 cm. in circumference.

Shape: Cup-shaped upon first opening and flattening as the tepals recurve during the second day.

Tepalage:

*Number.*—Six, hexagonally arranged.

*Shape.*—Elliptical with attenuate base.

*Size.*—Outer tepals average about 3 cm. wide and the inner tepals average about 4.5 to 5 cm. wide.

*Color.*—The flowers are distinguished by the golden orange coloration of their tepals, the basic color being Orange, 25A-B. This deepens into Orange, 28B, in an area about 1 cm. wide and 2 cm. long at the center of each tepal just above the nectaries. The nectaries are overlaid with white pubescence.

*Spotting.*—The tepals are unspotted.

*Appearance.*—The flower is shiny.

*Longevity.*—The tepals stay on the stems for about three weeks.

*Color changes.*—The flower may become slightly more orange and less gold as it ages depending upon light levels. Usually there is only a slight color change if the light levels are adequate for cut flower maintenance.

Pedicel:

*Length.*—Averages about 4 to 8 cm.

*Character.*—Sturdy and ascending up to about 60 degrees from the horizontal.

*Color.*—Medium to dark green.

Fragrance: None.

Disease resistance: The flower and plant are resistant to disease and, in particular, they are resistant to Fusarium bulb rot and Botrytis blight.

Lasting quality: The flower is long lasting.

REPRODUCTIVE ORGANS

Stamens:

*Number.*—Six.

*Arrangement.*—Typical of genus Lilium.

*Filaments.*—Length: About 5 cm. Color: Soft Orange, 28B-C.

*Anthers (dehisced) and pollen.*—Color: Orange-Red, 34B.

Pistil:

*Number.*—One.

*Length.*—About 5 cm.

*Stigma.*—Size: Medium, about 2 to 3 mm. wide. Color: Soft plum, Greyed Red, 180B-C.

Character of ovary: The ovary is characteristic of the genus Lilium.

THE FRUIT

Fertility: The fruit is fertile.

Shape: Ovoid.

Color at maturity: Soft brown, sometimes overlaid with soft plum.

This new lily variety most nearly resembles 'Croesus' but it has a deeper golden-orange coloration at the center of the tepals and it lacks any spotting; also, it has a more compact inflorescence than does 'Croesus'. This new variety also resembles its sister seedling 'Foxtrot' (patent pending) and the variety 'Quickstep' (patent pending). The new plant has longer stems, a deeper color, broader and less "clawed" tepals, and a less recurved and more "cup-shaped" flower form than does 'Foxtrot'; and it requires a longer forcing time. The new plant has lighter and slightly shorter stems, broader tepals, and requires a shorter forcing time than does 'Quickstep'; it also has fluted tepal margins, in contrast with the smooth margins of 'Quickstep'.

I claim:

1. The new and distinctive variety of Asiatic lily plant and parts thereof, substantially as herein shown and described, characterized in particular by its unspotted, broad tepalled, rich golden-orange flowers with fluted tepal margins; and by the excellence of its flower form and its versatility both as a garden plant and as a cut flower variety well suited to forcing into flower out-of-season.

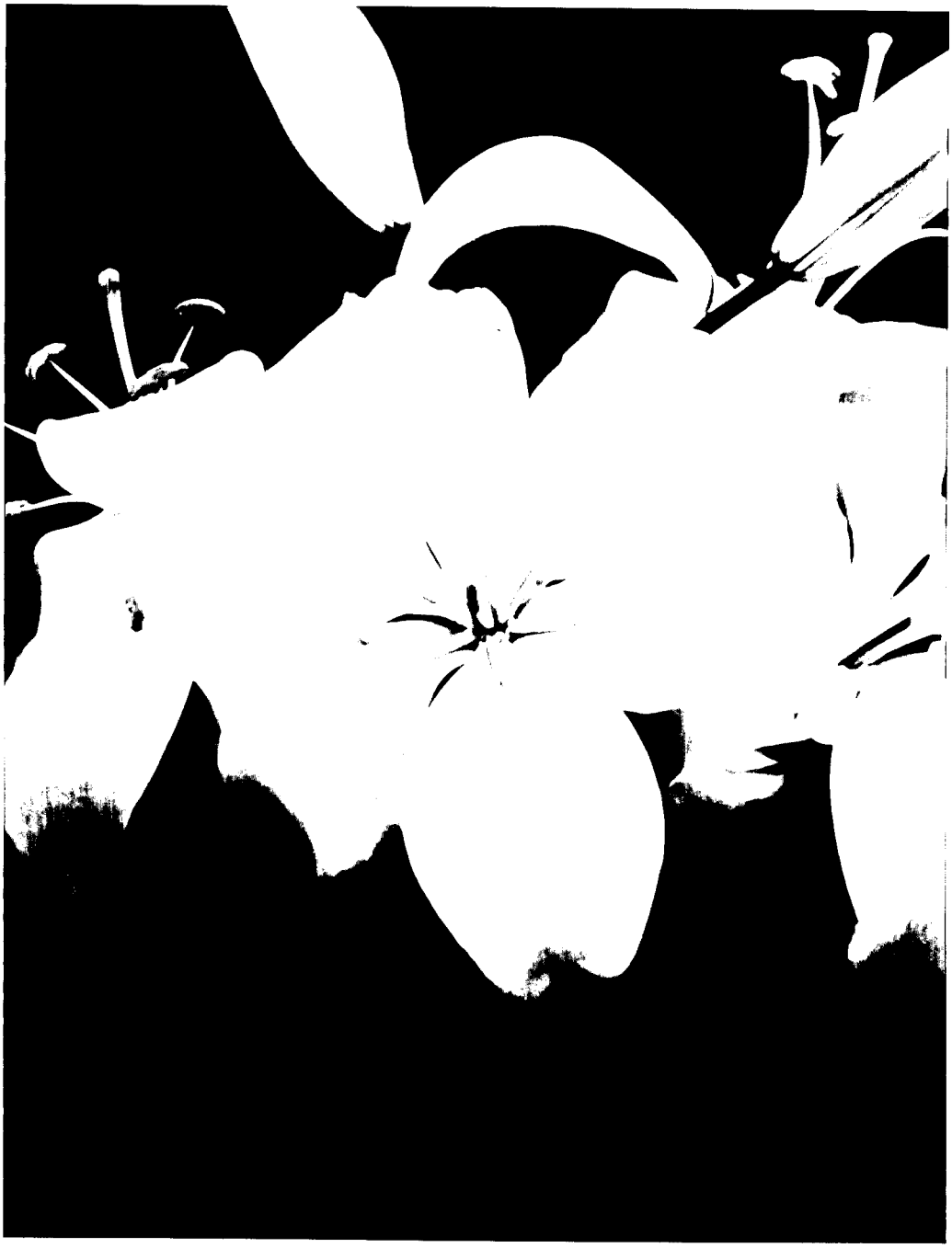

* * * * *